United States Patent
Büttner et al.

(10) Patent No.: US 10,800,130 B2
(45) Date of Patent: Oct. 13, 2020

(54) FLEXIBLE PCM SHEET MATERIALS

(71) Applicant: smartpolymer GmbH, Rudolstadt (DE)

(72) Inventors: Dirk Büttner, Berlin (DE); Angelo Schütz, Rudolstadt (DE); Martin Geissenhöner, Rudolstadt (DE)

(73) Assignee: smartpolymer GmbH, Rudolstadt (DE)

( * ) Notice: Subject to any disclaimer, the term of this patent is extended or adjusted under 35 U.S.C. 154(b) by 140 days.

(21) Appl. No.: 15/311,633

(22) PCT Filed: May 19, 2015

(86) PCT No.: PCT/EP2015/061022
§ 371 (c)(1),
(2) Date: Nov. 16, 2016

(87) PCT Pub. No.: WO2015/177168
PCT Pub. Date: Nov. 26, 2015

(65) Prior Publication Data
US 2017/0087799 A1    Mar. 30, 2017

(30) Foreign Application Priority Data
May 19, 2014   (DE) .................. 10 2014 007 219

(51) Int. Cl.
*B32B 19/00* (2006.01)
*B32B 1/00* (2006.01)
(Continued)

(52) U.S. Cl.
CPC .................. *B32B 3/16* (2013.01); *B32B 1/00* (2013.01); *B32B 3/00* (2013.01); *B32B 3/02* (2013.01);
(Continued)

(58) Field of Classification Search
CPC .... B32B 3/16; B32B 3/12; B32B 3/08; B32B 3/06; B32B 3/02; B32B 3/00;
(Continued)

(56) References Cited

U.S. PATENT DOCUMENTS 5,178,835 A  *  1/1993  Uekusa ............ G01N 35/00009
                                                    422/63
5,362,819 A  *  11/1994  McBain ................. C08G 81/00
                                                    525/404
(Continued)

FOREIGN PATENT DOCUMENTS

DE              10022287 A1     5/2000
DE       10 2012 218378 A1     4/2014
(Continued)

*Primary Examiner* — Michael Zhang
(74) *Attorney, Agent, or Firm* — ProPat, L.L.C.; Cathy Moore

(57) ABSTRACT

The invention relates to flexible PCM sheet materials having a high latent thermal energy storage density for the purpose of heat management. The flexible PCM sheet material includes a flexible supporting structure and phase-change-material elements arranged thereon separately in a specific geometry. The phase-change-material elements are geometrically defined structures composed of polymer-bound phase-change material. The flexible PCM sheet materials are characterized by a high latent heat storage capacity and optimized thermal conductivity, are dimensionally stable even in the event of temperature changes and after phase transitions, can be rolled, folded, wound, or cut to size without problems, and can be transported, stored, processed, or used in a single layer or in multiple layers.

16 Claims, 2 Drawing Sheets

(51) Int. Cl.

| | |
|---|---|
| B32B 3/00 | (2006.01) |
| B32B 5/00 | (2006.01) |
| B32B 3/12 | (2006.01) |
| B32B 27/36 | (2006.01) |
| B32B 15/00 | (2006.01) |
| A61F 7/02 | (2006.01) |
| A61K 9/70 | (2006.01) |
| B32B 3/16 | (2006.01) |
| B32B 27/08 | (2006.01) |
| B32B 27/30 | (2006.01) |
| B32B 27/32 | (2006.01) |
| B32B 3/02 | (2006.01) |
| B32B 7/04 | (2019.01) |
| B32B 27/06 | (2006.01) |
| B32B 7/00 | (2019.01) |
| B32B 3/08 | (2006.01) |
| B32B 5/02 | (2006.01) |
| B32B 19/04 | (2006.01) |
| B32B 7/12 | (2006.01) |
| B32B 27/34 | (2006.01) |
| B32B 3/06 | (2006.01) |
| B32B 27/00 | (2006.01) |
| B32B 23/00 | (2006.01) |
| B32B 9/00 | (2006.01) |
| B32B 27/18 | (2006.01) |
| B32B 27/28 | (2006.01) |
| B32B 15/08 | (2006.01) |

(52) U.S. Cl.
CPC ............... *B32B 3/06* (2013.01); *B32B 3/08* (2013.01); *B32B 3/12* (2013.01); *B32B 5/00* (2013.01); *B32B 5/02* (2013.01); *B32B 5/022* (2013.01); *B32B 7/00* (2013.01); *B32B 7/04* (2013.01); *B32B 7/12* (2013.01); *B32B 9/00* (2013.01); *B32B 15/00* (2013.01); *B32B 15/08* (2013.01); *B32B 19/00* (2013.01); *B32B 19/04* (2013.01); *B32B 19/048* (2013.01); *B32B 23/00* (2013.01); *B32B 27/00* (2013.01); *B32B 27/06* (2013.01); *B32B 27/08* (2013.01); *B32B 27/18* (2013.01); *B32B 27/28* (2013.01); *B32B 27/30* (2013.01); *B32B 27/302* (2013.01); *B32B 27/32* (2013.01); *B32B 27/34* (2013.01); *B32B 27/36* (2013.01); *A61F 7/02* (2013.01); *A61K 9/7023* (2013.01); *B32B 2262/00* (2013.01); *B32B 2305/00* (2013.01); *B32B 2305/02* (2013.01); *B32B 2307/30* (2013.01); *B32B 2307/546* (2013.01); *B32B 2457/00* (2013.01); *B32B 2605/00* (2013.01)

(58) Field of Classification Search
CPC ......... B32B 27/06; B32B 27/36; B32B 27/34; B32B 27/32; B32B 27/302; B32B 27/30; B32B 27/18; B32B 27/08; B32B 27/28; B32B 27/00; B32B 1/00; B32B 23/00; B32B 19/048; B32B 19/04; B32B 19/00; B32B 15/08; B32B 15/00; B32B 9/00; B32B 7/04; B32B 7/00; B32B 5/022; B32B 5/02; B32B 5/00; B32B 2305/00; B32B 2307/30; B32B 2307/546; B32B 2262/00; B32B 2605/00; B32B 2457/00
See application file for complete search history.

(56) References Cited

U.S. PATENT DOCUMENTS

| | | | | |
|---|---|---|---|---|
| 5,718,835 | A | * | 2/1998 | Momose ............... C09K 5/063 106/271 |
| 6,319,599 | B1 | | 11/2001 | Buckley |
| 6,451,422 | B1 | * | 9/2002 | Nguyen ................ B32B 27/12 106/270 |
| 2002/0164474 | A1 | * | 11/2002 | Buckley ................. A61F 7/02 428/308.4 |
| 2004/0033743 | A1 | * | 2/2004 | Worley ............. A41D 31/0038 442/59 |
| 2010/0015430 | A1 | * | 1/2010 | Hartmann ................ B32B 7/02 428/323 |
| 2011/0193008 | A1 | | 8/2011 | Fieback et al. |
| 2012/0064327 | A1 | * | 3/2012 | Schutz ............... B29C 47/0021 428/220 |

FOREIGN PATENT DOCUMENTS

| | | | | |
|---|---|---|---|---|
| EP | 0412021 | A1 | * 2/1991 | ............ C09K 5/063 |
| GB | 2495938 | A | 5/2013 | |
| WO | WO-2007039221 | A1 | * 4/2007 | ............... E04B 9/02 |

* cited by examiner

FLEXIBLE PCM SHEET MATERIALS

CROSS-REFERENCE TO RELATED APPLICATIONS

This application is being filed under 35 U.S.C. § 371 as a National Stage Application of International Application No. PCT/EP2015/061022 filed May 19, 2015, which claims priority to the following parent application: German Patent Application No. 10 2014 007 219.3, filed May 19, 2014. Both International Application No. PCT/EP2015/061022 and German Patent Application No. 10 2014 007 219.3 are hereby incorporated by reference herein in their entirety.

FIELD OF THE INVENTION

The invention relates to flexible PCM sheet materials with high latent thermal energy storage density for use in heat management. The flexible PCM sheet material is formed from a flexible carrier structure and phase change material elements disposed thereon separately in specific geometry. The phase change material elements themselves comprise geometrically defined structures of polymer-bound phase change material. The flexible PCM sheet materials are distinguished by high latent thermal storage capacity and optimized thermal conductivities, are dimensionally stable even during temperature changes and after phase transitions, and can be readily rolled, folded, wound or cut to size, and transported, stored, processed or used in either single-ply or multi-ply form.

BACKGROUND OF THE INVENTION

US 20020164474 discloses flexible thermal regulation materials which find use in socks, as footwear linings or other articles of clothing. In order to prevent bleeding of the phase change materials (PCM) in the liquid phase, these PCM are encapsulated and distributed in a flexible matrix material. Another reason for the encapsulation is to prevent the formation of inflexible, rigid PCM aggregates on cooling. If not operating with encapsulation, the PCM are firmly absorbed in absorbents or superabsorbents, such as polyacrylic or carboxylmethylcellulose. The matrix material is preferably a flexible polymer or a polymeric foam. Other embodiments relate to laminates having insulating layers externally and a PCM-containing layer in the middle, or an integrated structure for which first a polymer layer is cast and is partially vulcanized, then a $2^{nd}$ layer, enriched with PCM, is cast and is likewise partially vulcanized, and thereafter a $3^{rd}$ layer of matrix material is cast thereon, and the assembly is completely vulcanized. The disadvantage of this solution is that with liquid/solid PCM encapsulation is necessary, the capsules cannot take on any desired shapes, or can be deformed arbitrarily and the overall assembly is limited in its flexibility. GB 2495938 describes an energy storage system wherein a multiplicity of capsules with PCM material are fixed on or partly in a carrier. The carrier may be rigid (plate) or flexible (sheet). The capsules are formed of polymeric (PVC) or metallic (aluminum) material. For improving the thermal conductivity, the PCM material is mixed with graphite or metal powders. The capsules may contain the same PCM material or different PCM materials. Either the capsules are fixed on the carrier or the carrier has recesses (depressions) for the PCM; the PCM is filled into the recesses, and lastly the filled recesses are sealed. A disadvantage here again is that the PCM material must be encapsulated and the flexibility is limited. Moreover, as in the case of US 20020164474, the flow resistance during loading and unloading thermal quantities with liquid or gaseous thermal carrier media is very high and hence hinders thermal transmission. On account of the necessary encapsulation described, a lot of mass and volume for the PCM is lost, thereby greatly reducing the overall capacity and leaving hardly any significant capacities within the system as a whole. Should the encapsulation suffer leakage, the liquefied PCM comes into contact with its environment. Sheet materials of this kind can also not be simply brought by cutting into the correct shape. The frequency of damage is a statistical variable which cannot be predicted. In the case of a too thin wall, for instance, there may be complete failure of the system. If, on the other hand, the thickness of the jacketing layer selected is too great, the abovementioned scenario of enthalpy reduction occurs.

In the case of Patent US 2002164474, the fundamental function of the PCM that of thermal conduction. The described introduction into open and/or closed-cell foams creates systems which are very sluggish in thermal terms; the very low surface area and poor thermal conduction mean that no improvement is achieved here by convection.

If a macroencapsulated PCM (e.g., plastic-jacketed) is adhered on a flexible matrix, it is always the (fixed) size of this element that determines the bending and minding radius and also the ability for trimming. A macroencapsulation cannot be cut, since the contents emerge. This also affects damage in use (e.g., installation into a wall).

DE 10022287 describes a knitted 3D spacer fabric having particles of a latent heat storage material disposed between the plies. The pressing of unencapsulated PCM particles into openings in a layer of the (knitted) spacer fabric is described. In order to prevent that these PCM particles fall out in the course of use or during washing, the layer containing PCM particles is lined with a liner having smaller openings than the size of the PCM particles, or with a film. Since the PCM particles are not firmly joined to the spacer material, the latter material cannot be cut to size arbitrarily. Because the spacer material as the carrier material has a number of millimeters of height, it is not arbitrarily flexible. The cited knitted spacer fabric is readily rollable only if it is still open-cell on one side. If the open chambers are sealed (surface-bonded) after having been filled with PCM particles, it can no longer be coiled up. The winding core is very much greater in the case of knitted spacer fabrics in comparison to the diameter of a PCM particle. Moreover, the loading density with the PCM particles is limited by the number of openings, and the accessibility of the PCM particles to receive flows of liquid or gaseous media is very limited.

SUMMARY OF ADVANTAGEOUS EMBODIMENTS OF THE INVENTION

The object is to provide a completely flexible, thermoregulating composite material which operates without encapsulation of the PCM, remains dimensionally stable even on temperature changes and phase transitions, and possesses optimized capacity for heat transmission as a result of the special geometrical variable arrangement of the shaped PCM elements on the sheet material. Moreover, this composite material shall be cutable to size, rollable, and stackable, and for improved thermal transmission the permeability for liquid and gaseous media shall be controllable.

DETAILED DESCRIPTION OF ADVANTAGEOUS EMBODIMENTS OF THE INVENTION

Figure 1:
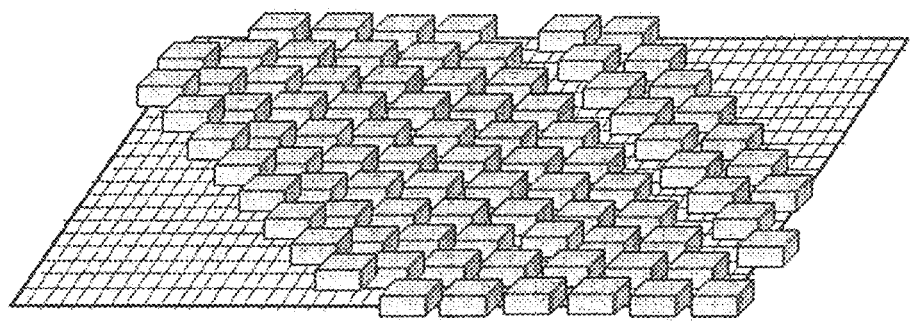
FIG. 1 is a schematic illustration of an exemplary embodiment comprising a netlike carrier having cuboid PCM casting.

The object is achieved by firmly fixing a plastified mass of a polymer-bound phase change material in geometrically defined structures on a carrier structure. The fixing here is accomplished such that the melt-liquefied, polymer-bound phase change material (abbreviated hereinafter to PCM) is applied to the carrier structure as spherical, square, rectangular or polygonal shaped elements having a thickness of 1 to 10 mm, preferably 1 to 5 mm, by injection molding, spray application, spreading or unpressurized casting by means of a forming device, in continuous or discontinuous operation. These spherical or polygonal shaped elements of polymer-bonded phase change material (PCM) are hereinafter referred to as PCM polymer castings. The carrier structures are substantially two-dimensional, meaning that the height of these structures is negligible in comparison to their length and width. Advantageous carrier structures prove to be woven fabrics, very preferably those having a large mesh size, made of polyamide, polyester, polypropylene, carbon fibers, metallic fibers or glass fibers, or natural fibers (cotton, rayon-viscose fibers) and fiber blends of these stated fibers. Other possible carrier structures composed of these materials are textile structures such as nonwovens, knitwear, tulle, knitting, braids, netlike fabrics of fibers or yarns or slit films. Films or membranes are possible as well, preferably porous, perforated or braided structures. The carrier structure fulfills mechanical functions such as improving the tensile strength of the sheet material, and, as a factor, determines the degree of flexibility and the flow-permeability. It may be configured in the form of a thermal or electrical conductor, e.g., as resistance heating, plastically deformable matrix or else in fully flexible form. Where electrical conductors or semiconductors are used, it is possible to exploit the Peltier effect as well as the thermal storage effect of the PCM materials. The separate arrangement of the polymer-bound. PCM polymer castings, and also the stretchability and adaptability of the carrier structure, especially in the case of a large-mesh structure, produce dimensional stability of the flexible PCM sheet material, even on phase change of the PCM. The PCM polymer castings are firmly joined, bonded or fused to the carrier structure, and are fixed superficially or penetrate partially into the carrier structure.

The material and the construction of the carrier structure determine whether the PCM sheet material has an open structure with which the PCM is able to fuse or additionally enhances its fixation enclosing the fibers. The flow-permeability also makes it easier to connect to other shaped elements, by casting resin or adhesive, for example. The size of the PCM elements is a factor in determining the flexibility, while for thermal transport/storage it is primarily the PCM material and the PCM layer thickness that are critical. Thermal transport may also be influenced by the choice of the material for the carrier structure, by using, for example, thermally conducting materials, or else by adjusting the flow-permeability of the sheet material. The flow-permeability for liquid and gaseous thermal transfer media (water, coolant, air, etc.) through this PCM sheet material and products produced from it (stacked form, roll form, etc.) can be tailored precisely in targeted fashion according to the invention by the packing density with shaped PCM elements, the lateral distance between the fixed shaped PCM elements, the distance between a plurality of plies of PCM sheet material, and also the geometric structure of the shaped elements themselves. By the flexible PCM sheet materials obtained accordingly, a PCM product is provided which firstly retains its dimensional stability under thermal stressing in the phase change temperature range, secondly can be folded, rolled, wound or cut to size for any of a wide variety of constructional applications of PCM materials, and, by virtue of its geometric carrier structure with PCM polymer castings arranged separately thereon, is able in particular to ensure unhindered flow passage of air, water and/or other thermal carrier media during loading and discharging of the stored thermal enthalpies in the PCM sheet material. According to the invention the foldability or rollability of the plies of PCM sheet material is facilitated by the PCM shaped elements being fixed firmly on the carrier sheet: materials with precise geometry, preferably in a linear row, with little edge spacing. The PCM sheet material, which according to the invention is produced preferably in the form of continuous PCM shaped element sheet materials, is preferably cut into appropriate sizes along the intermediate spacings in these rows of PCM shaped elements. However, even destructive cutting of the PCM polymer castings does not lead to any bleeding of the PCM material and hence also does not lead to any impairment in use.

The smaller the distance of the PCM polymer castings from one another, the greater the thermal capacity. The distances ought not to be below 0.5 mm, since otherwise there may be instances of surface sticking of the PCM polymer castings to one another during storage, especially if the phase change temperature is exceeded. A distance of 2 mm has proved to be an optimum in terms of production and of use.

Preferably the thickness (height) should not exceed 5 mm, and more preferably this thickness is 5 mm unless the application dictates otherwise. Up to 5 mm, the PCM can be almost fully utilized thermally; at more than 5 mm in height, it no longer participates in the energy exchange process, caused by surface cooling of the sides and poorer thermal conduction.

The plastified mass of the polymer-bound phase change material comprises at least 2 carrier polymers, selected from the group of styrene-containing block copolymers, preferably styrene-ethylene-butadiene-styrene block copolymers and/or styrene-ethylene-propylene block copolymers (SEBS and SEEPS, respectively, and also comprises a styrene-free component, selected from the group of polyolefin copolymers with random distribution, preferably an ethylene-butylene copolymer component. The polyolefin copolymer component has a high degree of crystallinity, preferably in the range from 15 to 30%. The ethylene content is preferably about 35 to 45% by weight, more preferably about 40% by weight. The mass possesses a low melting point (preferably about 70 to 90° C., more preferably 75 to 85° C., determined in each case by DSC at 10 K/min heating rate) and also low viscosity values (the MFI at 230° C. under a load of 2.161 kg is preferably about 0.5 to 5.0 g/10 min, determined according to DIN ISO 1133). The molar mass is preferably in the range from 250 000 to 500 000 g/mol. One of the purposes of this is to minimize the processing temperature for the casting compound, preventing evaporation of the PCM material during application to the carrier structure. The processing temperature for the casting compound is situated in a range of 100-140° C., preferably at about 120° C. Styrene-containing block copolymers terminated with hydroxyl groups are used in particular when the PCM materials in question are polar materials which themselves have hydroxyl and/or carboxyl groups.

The proportion of the styrene blocks in the styrene-containing block copolymers is usefully about 25 to 35% by weight, preferably about 30% by weight. By the use of a styrene-containing block copolymer, terminated with hydroxyl groups, in a proportion of 3 to 35% by weight in the styrene block copolymers, a PCM polymer mixture is obtained which prevents escape or exudation of the PCM components, such as natural and synthetic paraffins, low-melting alkanes, fatty alcohols, fatty acids, long-chain dialkyl ethers, polyethylene glycols, highly crystalline PE waxes, which improves adhesion of the PCM polymer mixture to the usually polar carrier structure, and which at the same time promotes the homogeneous incorporation of specific inorganic additives such as metals or metal oxides, preferably zinc oxide, or such as graphite, carbon black, and multiwall carbon nanotubes, and also of organic additives, into the PCM polymer mixture. These additives are used in order to improve the thermal conductivity and hence the heat exchange. Furthermore, the density of the PCM can be adjusted using metal oxides, pure metal powders, ceramic substances, etc which have a substantially higher density than 1 g/cm$^3$. This is necessary for applications in which the PCM (density approximately 0.9) must not float in liquid media (e.g., water). Other possible additives include thermochromic dyes (preferably in a proportion of 0.1 to 3% by weight) which operate in the range of the phase change temperature and indicate the progress and/or homogeneity of the phase change process. Further possible additions include flame retardants, in the PCM or/and in the matrix.

Another effect of the polar terminal OH groups in the styrene-containing block copolymers is the improved homogenization of additives, more particularly of zinc oxide, carbon black, graphite or carbon nanotubes, in the other carrier polymers of the carrier polymer composition. Through the use even of small amounts of 3 to 8% by weight of polyolefin copolymers in the carrier polymer matrix mixture, a much lower processing temperature is possible in the production of the PCM polymer compounds, and also during the actual application of the PCM polymer castings to the textile carrier were in accordance with the invention. On the other hand, these copolymers affect a greater volume expansion of the overall polymer matrix at the phase change temperature of the PCM, which is lower in the case of purely styrene-containing triblock copolymers. The effect of a greater volume expansion of the polymer matrix at the phase change temperature is reduced exudation of liquefied phase change material.

The ratio of styrene-containing block copolymers to the polyolefin copolymers may vary within a range from 10:1 to 1:1, and is preferably 4:1 to 2:1.

In order to improve further the exudation behavior of the phase change material, and to get a better surface feel, the PCM polymer castings may be covered with a thin, stretchable layer in the form of a film or foil, or with a textile fabric. This may be a layer of polymer, of metal or of ceramic. The thickness of the covering is 3 to 10 µm. Particular preference in this context is given to a foil layer made of Ultramid 1C polyamide. Prior surface etching of the butadiene portion of the carrier polymer with an alkaline permanganate solution results in very good adhesion of the Ultramid 1C film on the PCM polymer castings.

The invention relates, furthermore, to flexible PCM sheet materials which can be folded and rolled in order to obtain geometric volume elements or multi-ply textile PCM sheet materials through which air, water or other liquid thermal carrier media can easily flow around the PCM polymer units, so that coupling in and coupling out of thermal energy take place very rapidly. These flexible PCM sheet materials consist of 1 to 10% by weight of carrier structures and 90 to 99% by weight of the polymer-bound phase change material. The polymer-bound phase change material comprises 10 to 30 weight % of carrier polymers and 70 to 90 weight % of PCM. The polymer-bound phase change material may additionally contain 5 to 25% by weight of organic and/or inorganic additives, based on the weight of the overall casting material consisting of PCM, polymers, and additives.

At the phase transition temperature of the phase change material, the flexible PCM sheet materials of the invention have a thermal storage enthalpy of up to 250 J/g and a weight per unit area of 1 to 4 kg/m$^2$. The weight per unit area is determined by the interstices of the PCM polymer casting points on the carrier structure, by the height of the cast-on polymer elements, by the nature and amount of the additives used, and also by the pure basis weight of the textile carrier structure itself. The thermal storage enthalpy depends significantly on the nature of the PCM used, on the proportion of the PCM in the polymer-bound PCM, and also on the carrier structure (material and weight) and on the mass per unit, area of the polymer-bound PCM material and the thickness (height) of the PCM polymer castings. The thermal storage enthalpy per unit area of the PCM sheet material can be up to 1000 kJ/m$^2$.

The advantageous effect of the invention is that in its produced form, the PCM sheet material remains permanently elastic and formable. Via the arrangement, particle thickness, and shaping of the PCM elements joined firmly to the matrix material, it is possible to define winding radius and thermal storage capacity.

These flexible sheet materials provided with PCM polymer are suitable for the storage and regulation of heat and cold, especially in buildings management (cooling panels), heat-sink applications in electrical engineering, heat/cold management in vehicle construction, for the single-ply or multi-ply jacketing of pipelines, as internals in pipes, boxes, etc, wound and/or laid in planar plies one on top of another, through which flows of air or water pass. The applications include, for example, the thermal conditioning of air. Stacked or rolled (for pipes) sheet materials would fill out corresponding containers and function as heat exchangers. Further possible applications lie in the thermal conditioning of relatively large surfaces on, for example, machines. The structures there could be mounted simply and around any angle, curvature, etc.

Through the material and the construction of the carrier structure it is possible to introduce additional functions. Besides mechanical stabilizations, when using metallic carrier structures it will be possible to store "heat" or "cold" in the PCM using electrical resistance heating and/or by the Peltier effect.

In particular through the dimensional stability of the textile carrier structure in the temperature range of the phase change of the PCM polymer mixture applied to the carrier structure, it is possible to compensate the otherwise customary disadvantages of pure PCM polymer films and PCM polymer plates, where there has always been unwanted shrinkage and deformation in the phase change region.

To illustrate the invention, 4 drawings are attached.

Figure 2:
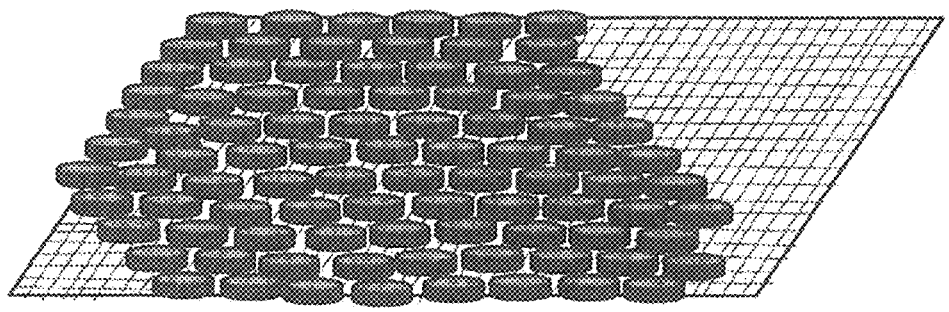
FIG. 2 is a schematic illustration of an exemplary embodiment comprising a carrier having cylindrical PCM castings.
Figure 3:
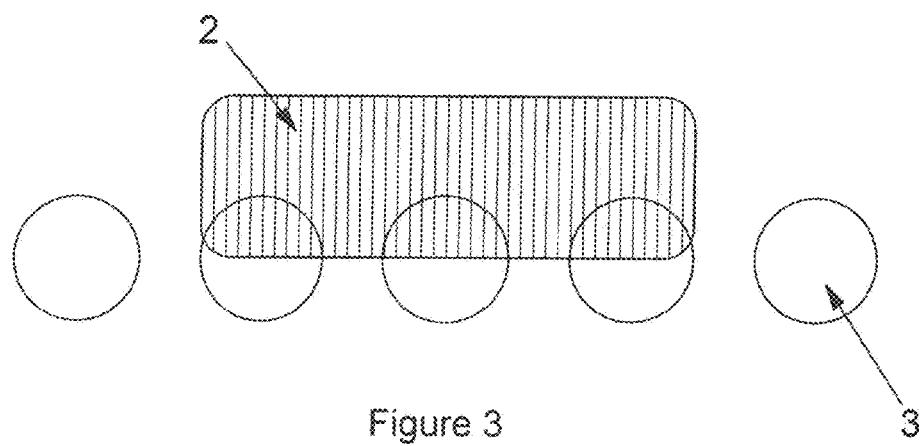
FIG. 3 is a cross-sectional schematic of an exemplary embodiment comprising a cast-on PCM polymer adhesively bonded to the carrier.
Figure 4:
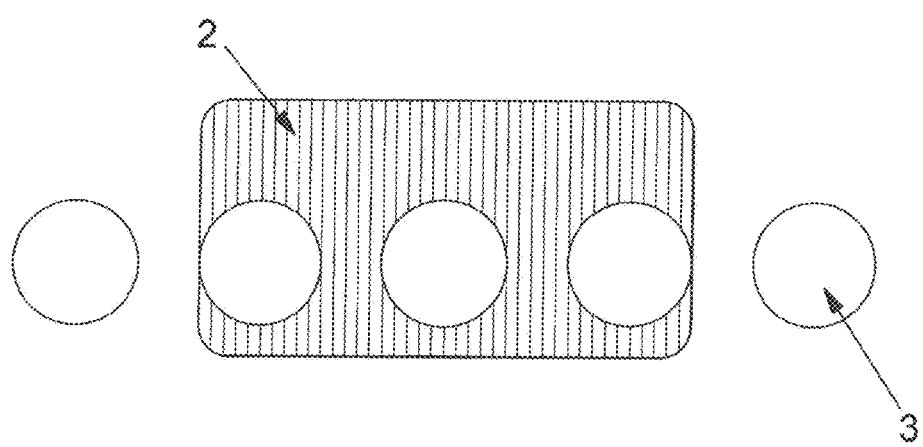
FIG. 4 is a cross-sectional schematic of an exemplary embodiment comprising a cast-on PCM surrounding fibers forming the carrier structure.

FIG. 1 shows schematically a netlike carrier structure (1) having cuboid PCM polymer castings (2) in parallel rows with constant, defined edge spacing. It is clearly apparent that, in view of the separate arrangement of the PCM polymer castings and the construction of the carrier structure, the capacity for liquids and gases to flow through is still good. In FIG. 2, the shape of the PCM polymer castings (2) is cylindrical, and the cylindrical PCM castings are again applied in parallel rows to the carrier structure. FIG. 3 shows a diagrammatic representation of a cross section through the carrier structure (3) with cast-on PCM polymer castings (2) in an adhesively bonded variant (e.g., filaments of natural/synthetic fibers, open-pore structures). The adhesive bonding relates to the capacity of the polymer-bound PCM material to generate a physical adhesion with the fiber surfaces on liquid melt application, and in other words to undergo bonding to the matrix on the surface, up to the point of complete or partial penetration, depending on the material of the carrier structure. FIG. 4 shows the schematic representation of a variant where the cast-on PCM polymer castings (2) surround the fibers (3) that form the carrier structure (positive connection). The plastified mass of the polymer-bound phase change material is able to penetrate the interstices of the carrier structure.

EXAMPLE 1

Using a ZSE 40 twin-screw extruder (from Leistritz) having an l/d ratio of 52:1, PCM polymer Pellets are first formed from the following starting materials:
- 80% by weight of PCM material (NACOL® ether 12 from sasol GmbH, long-chain dialkyl ether having a m.p. of 32° C.
- 10% by weight of styrene block copolymer SEEPS (polystyrene-b-poly(ethylene-ethylene/propylene)-b-polystyrene; SEPTON® 4055 from Kuraray Co. Ltd.)
- 5% by weight of OH-terminated styrene block copolymer (SEPTON® HG from Kuraray Co. Ltd.)
- 5% by weight of crystalline ethylene-butylene copolymer (type 6201 B from JSR Dynaron).

The extrusion die was connected via an adapter plate to the cutting head of a Gala underwater pelletizer (Gala Inc.). Pellets having a diameter of 4 to 5 mm were obtained.

The thermal storage capacity of the resulting pellets at the phase change temperature of the PCM with a switching temperature of 32° C. was 215 J/g.

The PCM polymer pellets were dried in a forced air drying cabinet at room temperature of 25° C. These pellets were then melted in a vertical single-screw extruder at 120° C., and the PCM polymer melt was supplied via an adapter to a die having multiple conical cuboidal or conical cylindrical openings, and the very low-viscosity PCM polymer melt was cast through the cuboidal or cylindrical openings onto a wide-meshed polyamide net 15 cm wide which was located directly beneath the multiple casting die. After the PCM polymer melt castings had cooled, the casting die was raised and the polyamide fabric was moved on, on a conveyor belt in each case, after which a further casting was carried out via the melt die.

By this way a polyamide net tape was obtained with PCM polymer blocks or PCM polymer cylinders applied closely thereto. The minimum distances between the PCM polymer blocks or PCM polymer cylinders were 1 mm. The height of the PCM polymer blocks or PCM polymer cylinders was 3 mm. The PCM polymer blocks had an edge length of 10 mm, and the PCM polymer cylinders had a diameter of 10 mm. The weight per unit area of the obtained polyamide fabric coated by the applied PCM polymer blocks or PCM polymer cylinders was 1950 and 1850 g/m$^2$, accordingly. The thermal storage capacity of the obtained polyamide fabric/PCM polymer assemblies was 200 J/g or, on an area basis, 390 KJ/m$^2$ and 370 KJ/m$^2$.

The cuboidal or cylindrical PCM polymer castings were joined very firmly to the woven polyamide fabric, even at the corresponding phase change temperature. The resultant mats of polyamide fabric and PCM polymer castings applied thereon (see FIGS. 1 and 2) could be wound up as cylinders or placed one on top of another in the form of multiple plies, and tests of loading with warm air and water showed that these mat constructions presented only a very low flow resistance to the entering and emerging thermal flows.

A particular advantage of the invention is that these PCM sheet materials can also be deformed in the cold state at any time to form rolled and stacked articles, even if using PCM castings with a high phase transition temperature. The stiffness of the relatively hard PCM castings is not a disruptive factor here, since the PCM sheet materials are very flexibly deformable at the edge intermediate spacings.

In a test chamber, a number of pieces of these polyamide fabric/PCM polymer mats were clamped firmly into two lateral frames and so arranged closely one behind the other. Hot air at 40° C. was passed through the test chamber, in order to load the polyamide fabric/PCM polymer mats with heat, and to melt the PCM they contained (NACOL® ether 12) at 32° C. At this phase transition temperature, the polyamide fabric/PCM polymer mats remained firmly clamped in, and did not sag or flap, as otherwise observed in the case of relatively thick PCM polymer films or PCM polymer plates.

EXAMPLE 2

Similar as indicated in example L PCM polymer pellets of the following composition:
- 80% by weight of PCM material (NACOL® ether 12 from Sasol GmbH, long_chain dialkyl ether)
- 10% by weight of styrene block copolymer SEBS (polystyrene-b-poly(ethylene/butylene)-b-polystyrene; SEPTON®8004 from Kuraray Co Ltd.)
- 5% by weight of OH-terminated styrene block copolymer (SEPTON® HG 252 from Kuraray Co. Ltd.)
- 5% by weight of crystalline ethylene-butylene copolymer (type 6201 B from JSR Dynaron)

were again produced in a Leistritz LSE 40 twin-screw extruder and downstream underwater pelletizer, then dried and applied to a wide-meshed polyamide fabric in a single-screw extruder using a special casting die.

The polyamide fabric with the PCM polymer castings (cuboidal or cylindrical) was then sprayed on both sides with a 5% by mass PA solution (of ULTRAMID® 1C) and the excess solvent was evaporated at room temperature. The thickness of the PA coating was about 5 μm. It proved to be a 100% harrier against the exudatin of PCM.

EXAMPLE 3

Much as indicated in example 1, PCM polymer pellets were again produced in the Leistritz ZSE 40 twin-screw extruder and downstream underwater pelletizer, then dried and subsequently applied to a wide-meshed polyamide fabric in a single-screw extruder, using a special casting die.

The material composition of the PCM polymer was altered in this case, however:
- 70 weight % of PCM material (NACOL® ether 12 from Sasol GmbH, long-chain dialkyl ether)
- 8% by weight of styrene block copolymer SEEPS (SEPTON® 4055 from Kuraray Co. Ltd.)
- 4% by weight of OH-terminated styrene Nock copolymer (SEPTON® HG 252 from Kuraray Co. Ltd.)
- 3% by weight of crystalline ethylene-butylene copolymer (type 6201 B from JSR Dynaron)
- 15 weight %; a zinc oxide powder Produced in the Leistritz ZSE 40 twin-screw extruder and downstream underwater pelletizer, then dried and applied to a wide-meshed polyamide fabric in a single-screw extruder, using a special casting mould.

The zinc oxide did not only improve the thermal conductivity of 0.2 W/mK (pure PCM polymer compound) to a value of 0.6 W/mK, but also resulted in a sharp reduction in the exudation of paraffin at phase transition, of the PCM.

The resulting polyamide fabric/PCM polymer mats were provided with an additional thin cotton coating by making up process, in order to meet requirements of various application-related aspects.

The thermal storage capacity of the resulting PCM polymer 2.0 pellets was 175 J/g, and the thermal capacity of the resulting polyamide fabric/PCM polymer sheet material was 160 J/g. On an area basis, this was 341 KJ/m² for castings having a PCM polymer block structure and 323 KJ/m² for PCM polymer castings having a cylinder structure.

EXAMPLE 4

For predetermined shapes and dimensions of the PCM polymer castings and thermal storage capacities of the PCM, the packing parameters of the carrier material by the PCM polymer castings can be calculated and presented in table form. With the aid of such tables it is possible to calculate the packing configuration required for an application. The calculations in this example were based on a synthetic paraffin having a phase change enthalpy of 248 kJ/kg*15 K. The compounding reduces this capacity by 20%. A full-area plate with a height of 5 mm based on this formula would have a capacity of 794 kJ/m².

This figure was employed as a baseline comparison figure for the calculation of the remaining fraction.

If, for example, a capacity of 600 kJ/m² is required (presettings: height: 5 mm, compound described above), the following is evident from table 1:
1. circular base form not possible
2. square base form offers the required capacity with a distance between 1-2 mm.
3. calculation:

600 (kJ/m²)/198 kJ/kg*15K=3.03 kg of PCM (of above specification)

3.03 kg of PCM/0.8 (g/cm³)=3.79 dm³=3790 cm³

3790 cm³/0.5 cm³=7580 pieces

√7580=87, rounded down to 87

100 (cm)/87=1.15 mm

The distance between the PCM castings must be 1.15 mm for a thickness of 5 mm and edge length of 1 cm in order to achieve a capacity of 600 kJ/m²

TABLE 1 comparison of the thermal storage capacity of carrier structures loaded with separate PCM polymer castings to form PCM sheet materials with continuous PCM coating. Casting height = 5 mm

| Distance between the PCM Particles in mm | Capacity/ m² in J | Form of base area of castings | Capacity in % relative to full-area coverage (5 mm) |
|---|---|---|---|
| 0.5 | 716 | suuare | 90 |
| 1 | 643 | square | 81 |
| 2 | 547 | square | 69 |
| 3 | 458 | square | 58 |
| 0.5 | 562 | circular | 71 |
| 1 | 505 | circular | 64 |
| 2 | 479 | circular | 54 |
| 3 | 360 | circular | 45 |

As can be seen from the table, a greater capacity per unit area can be achieved using square base areas. Circular base areas produce Smaller unit-area capacities. When staggered, these figures do become a little better, but do not achieve the same figures as the square areas.

The column "Capacity in % relative to full-area coverage" indicates how much capacity is left over with different geometries (square or circular) and distance dimensions relative to a full-area PCM layer.

Assumption of the height of the castings and height of the PCM layer is 5 mm; on reduction of the height, the capacity decreases linearly and is therefore not recorded in the table.

In the case of the loading figures in %, there are gentle jumps. These jumps are a result of the fact that, depending on element spacing, whole rows do no longer come about at the edge. In practice, they could be cut mechanically, and then the ratios would be linear. All other base geometries (e.g., triangle, rectangles, etc.) are situated in each case between the figures for square and circle, in terms of utilization of loading per unit area, and are therefore not listed further in the table.

The invention claimed is:

1. A flexible PCM sheet material with high latent thermal energy storage capacity comprising a flexible 2-dimensional carrier structure having separately arranged, geometrically defined structures of a polymer-bound phase change material applied on the surface thereof and connected firmly to the carrier structure,
   the phase change material being bound by at least two carrier polymers, of which at least one polymer is a styrene-containing block copolymer and at least one polymer is a styrene-free ethylene/butylene copolymer,
   wherein the sheet material is dimensionally stable even on phase change and is processable in rolled, folded, wound, cut-to-size or multi-ply form, and
   the geometrically defined structures have a cuboid or cylindrical shape and a thickness of 1 to 5 mm,
   and the polymer bound phase change material has a melt flow index at 230° C. under a load of 2.16 kg of about 0.5 to 5.0 g/10 min, determined according to DIN ISO 1133.

2. The flexible PCM sheet material as claimed in claim 1, wherein the carrier structure comprises webs, nonwovens, knitwear, knittings, braids of fibers or yarns or slit films, films or membranes.

3. The flexible PCM sheet material as claimed in claim 2, wherein the material of the carrier structure comprises polyamide, polyester, polypropylene, cellulose, carbon, metal, glass, natural fibers or mixtures of these materials.

4. The flexible PCM sheet material as claimed in claim 2, wherein the carrier structure comprises webs having a mesh size or porous or braided structures.

5. The flexible PCM sheet material as claimed in claim 1, wherein said PCM sheet material comprises 1 to 10% by weight of carrier structure and 90 to 99% by weight of geometrically defined structures of the polymer-bound phase change material applied to said carrier structure.

6. The flexible PCM sheet material as claimed in claim 1, wherein the polymer-bound phase change material comprises 10 to 30% by weight of carrier polymers and 90 to 70% by weight of phase change material.

7. The flexible PCM sheet material as claimed in claim 1, wherein said phase change material is liquefiable and said PCM sheet material contains 5 to 20% by weight of inorganic or organic additives, based on the weight of the polymer-bound phase change material.

8. The flexible PCM sheet material as claimed in claim 1, wherein said phase change material is liquefiable and said PCM sheet material is coated superficially with a layer 3 to 10 μm thick of polymeric, metallic or ceramic material or covered with a textile sheet comprising said polymeric, metallic or ceramic materials.

9. The flexible PCM sheet material as claimed in claim 1, wherein the polymer-bound phase change material has a weight per unit area of 1 to 4 kg/m².

10. The flexible PCM sheet material as claimed in claim 1, wherein said PCM sheet material is flow-permeable by liquid or gaseous thermal media.

11. A flexible PCM sheet material as claimed in claim 1, wherein the styrene-containing block copolymer comprises styrene-ethylene-butadiene-styrene or styrene-ethylene-propylene and a portion of the styrene-containing block copolymer is terminated with hydroxyl groups.

12. A flexible PCM sheet material as claimed in claim 11, wherein the portion of the styrene-containing block copolymer terminated with hydroxyl groups is 3 to 35% by weight of the styrene block copolymer.

13. A flexible PCM sheet material as claimed in claim 1, wherein the geometrically defined structures have a distance from one another ranging from 0.5 mm to 2 mm.

14. A flexible PCM sheet material with high latent thermal energy storage capacity comprising a flexible 2-dimensional carrier structure having separately arranged, geometrically defined structures of a polymer-bound phase change material applied on the surface thereof and connected firmly to the carrier structure,
the phase change material being bound by at least two carrier polymers, of which at least one polymer is a styrene-containing block copolymer and at least one polymer is a styrene-free ethylene/butylene copolymer,
wherein the sheet material is dimensionally stable even on phase change and is processable in rolled, folded, wound, cut-to-size or multi-ply form, and
the geometrically defined structures have a thickness of 1 to 5 mm,
wherein (i) the geometrically defined structures are applied in melt-liquified form, (ii) the styrene-containing block copolymer is either styrene-ethylene-butadiene-styrene or styrene-ethylene-propylene and (iii) the styrene-containing block copolymer and styrene-free ethylene/butylene copolymer are present in a ratio of 10:1 to 2:1.

15. The flexible PCM sheet material as claimed in claim 14, wherein the polymer bound phase change material has a melt flow index at 230° C. under a load of 2.16 kg of about 0.5 to 5.0 g/10 min, determined according to DIN ISO 1133.

16. A method for producing the flexible PCM sheet material with high latent thermal energy storage capacity as claimed in claim 1, comprising fixing a plastified mass of the polymer-bound phase change material firmly in geometrically defined structures on carrier structure, by applying the melt-liquefied, polymer-bound phase change material to the carrier structure as cuboid or cylindrical separate shaped elements by injection molding, spraying, spread-coating or unpressurized casting by means of a forming apparatus in a continuous or discontinuous process.

* * * * *